United States Patent

Aumueller et al.

[11] Patent Number: 5,118,859
[45] Date of Patent: Jun. 2, 1992

[54] PREPARATION AND PURIFICATION OF 2-HYDROXY-4-(2'-HYDROXYETHOXY)PHENYL ARYL KETONES

[75] Inventors: Alexander Aumueller, Deidesheim; Wolfgang Goetze, Maxdorf, both of Fed. Rep. of Germany

[73] Assignee: BASF Aktiengesellschaft, Ludwigshafen, Fed. Rep. of Germany

[21] Appl. No.: 600,728

[22] Filed: Oct. 22, 1990

[30] Foreign Application Priority Data

Nov. 3, 1989 [DE] Fed. Rep. of Germany ........ 3936592

[51] Int. Cl.$^5$ ............................................ C07C 45/00
[52] U.S. Cl. .................................... 568/315; 558/415
[58] Field of Search ...................... 568/315; 558/415

[56] References Cited

U.S. PATENT DOCUMENTS

| | | | |
|---|---|---|---|
| 4,341,905 | 2/1982 | Strege | 568/45 |
| 4,885,396 | 12/1989 | Hahn et al. | 568/315 |
| 4,978,797 | 12/1990 | Kim et al. | 568/315 |
| 4,980,512 | 12/1990 | Aumueller et al. | 568/315 |

FOREIGN PATENT DOCUMENTS 1186818  4/1970  United Kingdom ................ 568/315

Primary Examiner—Bruce Gray
Attorney, Agent, or Firm—John H. Shurtleff

[57] ABSTRACT

2-Hydroxy-4-(2'-hydroxyethoxy)phenyl aryl ketones I

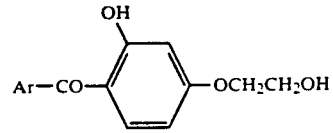

where Ar is substituted or unsubstituted aryl, are prepared by reacting 2,4-dihydroxyphenyl aryl ketones II

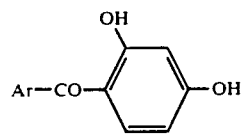

with ethylene carbonate in the presence of an alkali metal or alkaline earth metal salt of a carboxylic acid as catalyst and purified with sodium dithionite.

13 Claims, No Drawings

PREPARATION AND PURIFICATION OF 2-HYDROXY-4-(2'-HYDROXYETHOXY)PHENYL ARYL KETONES

The present invention relates to an improved process for preparing 2-hydroxy-4-(2'-hydroxyethoxy)phenyl aryl ketones of the formula I

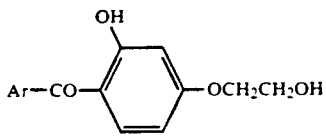

where Ar is substituted or unsubstituted aryl, by reacting a 2,4-dihydroxyphenyl aryl ketone of the formula II

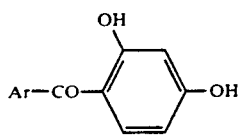

with ethylene carbonate in the presence of a catalyst. The present invention further relates to the purification of crude compounds I as obtained in industrial syntheses.

The preparation of compounds I, which are important for use as light stabilizers for plastics and coatings, by reacting compounds II with ethylene carbonate (1,3-dioxolan-2-one) with the aid of catalysts is known from various publications, in which the recommended catalysts are basic alkali metal or alkaline earth metal carbonates or alcoholates (U.S. Pat. No. 4,341,905) and quaternary ammonium salts (U.S. Pat. No. 4,885,396). However, these catalysts leave something to be desired, in the main because they require relatively long reaction times. Regardless of the nature of the catalyst and the ethoxylating agent, which may be ethylene oxide instead of ethylene carbonate, the products generally still need to be purified.

It is an object of the present invention to provide an improved process for preparing a compound I and also—independently of the method of preparation—a process for purifying said compound I.

We have found that this object is achieved by a process for preparing a 2-hydroxy-4-(2'-hydroxyethoxy)phenyl aryl ketone of the formula I

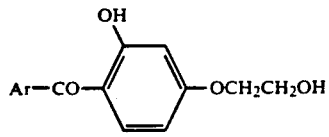

where Ar is substituted or unsubstituted aryl, by reacting a 2,4-dihydroxyphenyl aryl ketone of the formula II

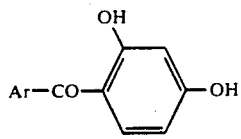

with ethylene carbonate in the presence of a catalyst, wherein the catalyst used is an alkali metal or alkaline earth metal salt of a carboxylic acid, and by a process for purifying a 2-hydroxy-4-(2'-hydroxyethoxy)phenyl aryl ketone of the formula I by treating a solution of the crude product of the formula I with sodium dithionite.

Suitable catalysts are basically the alkali metal and alkaline earth metal salts of all carboxylic acids, provided that in the case of polybasic carboxylic acids all the acid functions are present in salt form. Preferred compounds are the sodium and potassium salts of carboxylic acids such as aliphatic carboxylic acids of from 1 to 8 carbon atoms, for example formic, acetic, propionic, butyric, valeric, caproic, caprylic or capric acid, unsaturated fatty acids, for example stearic or oleic acid, aromatic carboxylic acids, for example benzoic acid or methylbenzoic acid, araliphatic carboxylic acids, for example phenylacetic acid, and hydroxycarboxylic acids, for example citric or tartaric acid. Particularly good results are obtained with the trisodium and tripotassium salts of nitrilotriacetic acid and the tetrasodium and tetrapotassium salts of ethylenediaminetetraacetic acid.

The amount of catalyst is not critical, but in general it is from 0.001 to 0.1 mol-eq per mole of acid function of II, preferably from 0.02 to 0.05 mol-eq. Larger amounts, say 0.25 mol-eq, do not in general produce any further benefits.

Suitable solvents for the reaction are solvents which are inert toward the reactants, for example ethers such as diethylene glycol dimethyl ether or anisole. However, it is advisable to carry out the reaction without a solvent.

Preferably, the reaction is carried out at from 100° to 210° C., in particular at from 120° to 200° C. To avoid secondary reactions and to obtain a satisfactory reaction rate, it is advisable to employ in particular the temperature range from 140° to 175° C.

In general, the ethylene carbonate may be used in an equimolar amount or in a slightly substoichiometric amount, but preferably it is used in a slight excess relative to the starting compound II. As a rule, the amount of ethylene carbonate used is from 0.95 to 1.5 mol per mole of 2,4-dihydroxyphenyl aryl ketone. Larger amounts are possible, but in general do not yield any further benefits. The reaction times are in general within the range from 2 to 12 hours.

There are no peculiar features to the method of working up. It may be effected by distillation or by crystallization.

Suitable starting compounds II are in principle all 2,4-dihydroxyphenyl aryl ketones. However, having regard to the use of the products I as light stabilizers, preference is given to those starting materials II in which the aryl is phenyl which is substituted by halogen such as fluorine, chlorine or bromine, by cyano or hydroxyl, by $C_1-C_8$-alkyl, eg. methyl, ethyl, propyl isopropyl or butyl, by $C_1-C_8$-alkoxy, eg. methoxy, ethoxy or propoxy, or by phenyl, phenoxy or benzyl. Preference is given to para-substituted phenyl and o-hydroxyphenyl. Particularly important compounds I and II are those in which Ar is unsubstituted phenyl, p-chlorophenyl, p-methylphenyl, p-methoxyphenyl, p-ethylphenyl, p-ethoxyphenyl, o-hydroxyphenyl or o-hydroxy-p-(2-hydroxyethoxy)-phenyl.

The starting 2,4-dihydroxyphenyl aryl ketones are known and can be obtained in a conventional manner, for example by Friedel-Crafts acylation of resorcinol with carbonyl chlorides.

Independently of the method of preparation, we have also developed a novel process for purifying 2-hydroxy-4-(2'-hydroxyethoxy)phenyl aryl ketones. The method of purification does not depend on the provenience of the products.

To purify the crude 2-hydroxy-4-(2'-hydroxyethoxy)phenyl aryl ketones, they are admixed with sodium dithionite in water, a $C_1$–$C_6$-alcohol or a mixture thereof, in the presence or absence of a protic acid and activated carbon.

The sodium dithionite is used in amounts of from 0.5 to 15% by weight, in particular from 5 to 10% by weight, based on the crude product.

Suitable solvents are water, saturated $C_1$–$C_6$-alcohols, preferably propanol, isopropanol, n-butanol, isobutanol, n-amyl alcohol, tert.-amyl alcohol, n-hexanol and particularly preferably methanol or ethanol, and also mixtures thereof.

In general it is advisable to boil the crude product I together with the sodium dithionite in from 2 to 5 times the amount of solvent for from 0.25 to 3 h. If necessary, a protic acid, in particular sulfuric acid, preferably from 10 to 20% by weight, based on the alcohol, and/or activated carbon, preferably from 0 to 20% by weight, in particular from 5 to 10% by weight, are added. The pure I is worked up in a conventional manner by crystallization, requiring no further comment.

The compounds I, which are obtained in a very pure form from the purification process, are used as UV absorbers in plastics and coatings, preferably wherever the self-color of an additive would be undesirable, as, say, in polystyrene and ABS and especially in clear polycarbonate.

EXAMPLES

Preparation of 2-hydroxy-4-(2'-hydroxyethoxy)phenyl aryl ketones

EXAMPLES 1 TO 8

418 g (2 mol) of 2,4-dihydroxybenzophenone were admixed with 193 g (2.2 mol) of ethylene carbonate and from 0.02 to 0.2 mol of catalyst, and the mixture was heated at 155° C. until gas evolution ceased. The liquid product was worked up in a conventional manner by crystallization and distillation. The details and the results of these experiments are shown in Table 1.

TABLE 1

| Catalyst Amount [mol] | Conversion % | Reaction time/h | Yield % | Purity % |
|---|---|---|---|---|
| According to the present invention | | | | |
| 1. Ethylenediaminetetraacetic acid, tetrasodium salt (0.02) | 99.5 | 7 | 95 | 97.5 |
| 2. Tripotassium citrate monohydrate (0.02) | 99.7 | 7 | 96 | 97.6 |
| 3. Nitrilotriacetic acid, trisodium salt (0.02) | 99.4 | 8 | 95 | 97.8 |
| 4. Sodium oleate (0.05) | 99.9 | 7 | 95 | 98.2 |
| 5. Sodium stearate (0.05) | 99.6 | 7 | 95 | 98.5 |
| Comparative experiments | | | | |
| 6. Tetrabutylammonium iodide (0.02) | 68.9 | 8 | 92 | 96.8 |
| 7. Potassium iodide (0.02) | 89.1 | 8 | 96 | 92.3 |
| 8. Sodium iodide (0.02) | 92.1 | 8 | 92 | 96.8 |

Purification of 2-hydroxy-4-(2'-hydroxyethoxy)phenyl aryl ketones

EXAMPLE 9

50 g of crude I as obtained in Examples 1 to 8 before working up were refluxed together with 2.5 g of sodium dithionite, 2.5 g of activated carbon and 10 ml of 2N sulfuric acid in a mixture of 100 ml of ethanol and 50 ml of water. After the insolubles had been filtered off in the heat, 50 ml of water were added to the filtrate, the filtrate was cooled, and the purified product was filtered off, washed with 200 ml of water and dried. The yield of pure product was 46.7 g.

Clear polycarbonate containing 0.2% by weight of the UV absorber had a Yellowness Index (ASTM D 1925) of 9.1. With the crude absorber its Yellowness Index was 11.8 and without any addition it was 7.1.

We claim:

1. A process for preparing a 2-hydroxy-4-(2'-hydroxy)phenyl aryl ketone of the formula

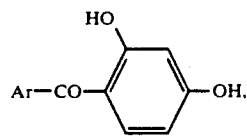

wherein Ar is unsubstituted phenyl or phenyl substituted by up to two substituents selected from the group consisting of halogen, cyano, hydroxy, p-(2-hydroxyethoxy), $C_1$–$C_8$-alkyl, $C_1$–$C_8$-alkoxy, phenyl, phenoxy and benzyl; said process comprising:

reacting a 2,4-dihydroxyphenyl aryl ketone of the formula

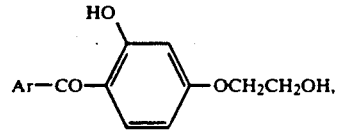

wherein Ar has the meaning given above, with ethylene carbonate in the presence of an alkali metal or alkaline earth metal salt of a carboxylic acid as a catalyst.

2. A process as claimed in claim 1, wherein the catalyst used is the sodium or potassium salt of a $C_1$–$C_{18}$-fatty acid, the trisodium or tripotassium salt of nitrilotriacetic acid or the tetrasodium or tetrapotassium salt of ethylenediaminetetraacetic acid.

3. A process for purifying a crude 2-hydroxy-4-(2'-hydroxyethoxy)phenyl aryl ketone of the formula I as obtained in claim 1, which comprises treating a solution of said crude product of the formula I with sodium dithionite.

4. A process as claimed in claim 3, wherein the solution of the crude product of the formula I is additionally treated with a strong mineral acid.

5. A process as claimed in claim 3 wherein the solution of the crude product of the formula I is treated with activated carbon.

6. A process as claimed in claim 4 wherein the solution of the crude product of the formula I is treated with activated carbon.

7. A process as claimed in claim 1, wherein Ar in the ketone II is selected from the group consisting of unsubstituted phenyl, p-chlorophenyl, p-methylphenyl, p-methoxyphenyl, p-ethylphenyl, p-ethoxyphenyl, o-hydroxyphenyl and o-hydroxy-p-(2-hydroxyethoxy)-phenyl.

8. A process as claimed in claim 1, wherein Ar in the ketone II is unsubstituted phenyl.

9. A process as claimed in claim 1, wherein the amount of catalyst used is from 0.001 to 0.1 mol-eq per mole of acid function of the ketone II.

10. A process as claimed in claim 1, wherein the reaction is carried out in the absence of inert solvents.

11. A process as claimed in claim 1, wherein the reaction is carried out at a temperature of from 100° to 210° C.

12. A process as claimed in claim 1, wherein the reaction is carried out at a temperature of from 120° to 200° C.

13. A process as claimed in claim 1, wherein the reaction is carried out at a temperature of from 140° to 175° C.

* * * * *